United States Patent [19]

Piani et al.

[11] Patent Number: 5,010,063

[45] Date of Patent: Apr. 23, 1991

[54] HEPARIN DERIVATIVES AND PROCESS FOR THEIR PREPARATION

[75] Inventors: Silvano Piani, Bologna; Gianfranco Tamagnone, Casafecchio di Reno; Raul R. Alpino, Bologna; Maria R. Milani, Trebbo di Reno; Marinella Fantuz, Bologna, both of Italy

[73] Assignee: Alfa Wasserman S.P.A., Alanno Scalo, Italy

[21] Appl. No.: 357,548

[22] Filed: May 26, 1989

[30] Foreign Application Priority Data

Jun. 10, 1988 [IT] Italy .................. 3504 A/88

[51] Int. Cl.$^5$ .................. A61K 31/725; C08B 37/10
[52] U.S. Cl. .................. 514/56; 514/54; 514/62; 514/822; 536/21
[58] Field of Search .................. 514/56, 62, 54, 822; 536/21

[56] References Cited

U.S. PATENT DOCUMENTS

| | | | |
|---|---|---|---|
| 3,016,331 | 1/1962 | Toccaceli | 536/21 |
| 3,065,140 | 11/1962 | Velluz et al. | 536/21 |
| 4,791,195 | 12/1988 | Bianchini et al. | 536/21 |
| 4,816,446 | 3/1989 | Feller et al. | 514/56 |
| 4,933,326 | 6/1990 | Bianchini et al. | 514/56 |

FOREIGN PATENT DOCUMENTS 0293539 12/1988 European Pat. Off. .
0347588 12/1989 European Pat. Off. .
2002406 2/1979 United Kingdom .

OTHER PUBLICATIONS

Ogren et al.; Chemical Abstracts 76:57073z (1972).
Fransson et al.; Biochem. J. 175:299-309 (1978).
Gatti et al.; Macromolecules 12(5):1001-1007 (1979).
Kosakai et al.; J. Biochem. 86:147-153 (1979).
Ayotte et al.; Carbohydrate Res. 145:267-277 (1986).

*Primary Examiner*—Ronald W. Griffin
*Assistant Examiner*—Nancy S. Carson
*Attorney, Agent, or Firm*—Bucknam and Archer

[57] ABSTRACT

New heparin derivatives having antithrombotic activity, also endowed with reduced hemorrhagic and anticoagulant activity, obtained by treating in a basic medium heparins of various origin, optionally in the presence of alkali metal salts and of a reducing agent.

The heparin derivatives obtained through this treatment show peculiar chimico-physical characteristics, like new signals at about 53 and 54 p.p.m. in the $^{13}$C-NMR spectrum and an increase of the specific rotatory power, compared to that of the starting heparins, to values between +50° to +90°.

Said structural modifications produce an improvement of the biological properties of the heparin, substantially keeping the antithrombotic activity while diminishing the hemorrhagic effect in vivo and the anticoagulant activity in vitro.

14 Claims, No Drawings

HEPARIN DERIVATIVES AND PROCESS FOR THEIR PREPARATION

BACKGROUND OF THE INVENTION

The present invention refers to new heparin derivatives having antithrombotic activity, also endowed with reduced hemorrhagic and anticoagulant activity, obtained by treating in a basic medium heparins of various origin, optionally in the presence of alkali metal salts and of a reducing agent.

It is known that heparin-like structures can be modified in various manners by treating them in a basic medium.

In European Publication EP No. 0133078, Mardiguian J. S., depolymerizes the heparin into oligosaccharides fractions containing from 4 to 20 saccharides units, by treating the benzyl ester of the heparin by means of an organic or inorganic base, at a concentration between 0.1 and 0.6 molar at a temperature between 20° C. and 80° C. Such depolymerization is accompanied by the formation of a double bond in the positions 4 and 5 of the uronic acid, detectable by U.V. absorption at 230 nm.

Hirano S. et al., Conn. Tissue Res., 3, 73-79, 1975 depolymerize the heparin and other glycosaminoglycans in strong basic medium, by using from 2 to 10 molar concentrations of sodium or barium hydroxide at temperatures higher than 80° C. In this way they get a strong depolymerization following the cleavage of the glucosidic bond between the position 1 of glucosamine units and the position 4 of adjacent uronic units. Moreover such deploymerization is accompanied by the formation of a double bond in the positions 4 and 5 of the uronic acid, detectable by means of an absorption at 225-230 nm in the U.V. spectrum.

Sampson P. and Meyer K., Proc. Nat. Acad. Sci. U.S.A., 68, 2329-2331, 1971, obtained a structural modification in the glucosamine unit with formation of 3,6-anhydroglucosamine by treating heparin with 1N sodium hydroxide in the presence of sodium borohydride at 80° C. for 7 hours.

The heparin derivatives object of the present invention totally differ from those described in the prior art. In fact they do not show the chimico-physical properties of the compounds obtained by Mardiguian J. S. and by Hirano S. et al., as it is shown by the average molecular weight which remains substantially unchanged, thus proving the lack of depolymerization, and by the lack of absorption at 225-230 nm in U.V. and of peaks corresponding to the resonances of the double bond in the $^{13}$C-NMR, which demonstrate the lack of the double bond in the positions 4 and 5 of the uronic acid. Moreover they do not even show the chimico-physical properties of the compounds isolated by Sampson P. and Meyer K. as the $^{13}$C-NMR spectrum of the compounds obtained in the present invention shows unchanged the position and the intensity of the signal of the carbon atom in position 6 of the glucosamine and shows unchanged the intensity ratio between the 6-sulfated carbon atom and the 6-desulfated carbon atom that should change in case of formation of 3,6-anhydroglucosamine because of the participation of the 6-sulfated carbon atom in the formation of the anhydroderivative.

SUMMARY OF THE INVENTION

The present invention relates to new heparin derivatives, to their therapeutic use in the treatment of the thrombotic diseases and to the process for their preparation by means of a chemical modification made in basic aqueous medium, optionally in the presence of salts and of a reducing agent, on heparins of various origin, commercial or purified by means of suitable treatments or depolymerized.

The new compounds having a modified heparinic structure possess chimico-physical properties, like specific rotatory power and $^{13}$C-NMR peaks, different from those of the starting compounds and also present a different biological activity as they show a better action specificity as they keep practically unchanged the antithrombotic properties while the hemorrhagic effect and the anticoagulant power are lowered. In particular they are characterized by the fact that they show two new signals in the $^{13}$C-NMR spectrum at about 53 and 54 ppm and an increase of the specific rotatory power, with respect to the starting heparins, with values between about +50° and about +90° in aqueous solution.

The chemical modification of the heparinic structure is obtained in aqueous medium at pH values higher than neutrality in the presence of a base, preferably of an alkali or an alkaline earth metal hydroxide, optionally in the presence of an alkali or alkaline earth metal salt and of a reducing substance, preferably sodium borohydride.

The reaction is carried out for a period of time between 0.5 and 24 hours, at a temperature between about 35° C. and about 70° C., using base concentrations between about 0.01N and about 1N and salt concentrations between 0 and about 1N, optionally in the presence of a reducing substance, like, for instance, sodium borohydride.

Alkali or alkaline-earth metal bases and salts are preferably used, mainly those of sodium, potassium, calcium, magnesium and barium.

The hydroxides of sodium, potassium and barium are the bases that can be advantageously used.

The acetates and chlorides of sodium, potassium, barium, calcium and magnesium and the sulfates of sodium, potassium and magnesium are the salts that can be advantageously used.

The process of modification of the heparinic structure is carried out by dissolving the heparinic material in an aqueous solution from about 0.01N to about 1N of a base of an alkali or alkaline-earth metal, optionally in the presence of a salt of an alkali or alkali-earth metal, at a concentration lower or equal than 1N, and of a catalytic amount of a reducing agent, and by thermostating the solution at a temperature between about 35° C. and about 70° C. for a period of time between about 0.5 hours and about 24 hours.

At the end of the reaction the solution is cooled to room temperature, brought to neutral pH and optionally purified, for instance by means of ion exchange resins or of dialysis, and lastly the modified heparin derivative is precipitated by adding from about 2 to about 4 volumes, preferably 2.5 volumes, of an alcohol containing from 1 to 3 carbon atoms, like for instance ethyl alcohol.

The modified heparins obtained in this process show some peculiar chimico-physical characteristics which are totally different from those derived from the alkali treatments known from the prior art. This is due to the reaction conditions used in the present invention where the values of the parameters, mainly as regards the base concentration, the temperature and the optional presence of a salt, are significantly different from those previously used.

The structural changes of the new heparin derivatives have been principally shown from the position and the relative intensity of the resonances in the $^{13}$C-NMR spectrum and also from the electrophoretic behaviour, from the increase of the values of the specific rotatory power and from the decrease of the sulfur content and of the sulfates/carboxyls ratio, being unchanged the carboxyls content.

The more characteristic changes in the structure of the new heparin derivatives have been checked through the study of the deep changes occurred in the $^{13}$C-NMR spectrum. These variations refer to some specific zones of the spectrum and involve both the appearance of new peaks and the modification of other peaks. Of noteworthy importance is the appearance of two new signals at about 53 and about 54 ppm and the shifts of the peaks corresponding to the carbon atom 1 of the iduronic and glucosaminic unit in the zone between 92 ppm and 102 ppm. The comparative check of the $^{13}$C-NMR spectra of the new compounds and of those of the starting compounds enable us to establish that some zones of the spectrum are unchanged and that consequently some portions of the heparinic structure have not been modified at all. In particular, the signals related to the position 6 of the sulfated or desulfated glucosamine unit have not been modified. Moreover, the peaks related to the position 2 of the glucosamine units, sulfated or acetylated, to the carboxy group of the iduronic acid and to the units of glucuronic acid, which in the heparin form an average of the 20% of the uronic residues, are unchanged.

The chimico-physical characteristics of the new heparin derivatives result the more modified the more drastic are the reaction conditions, as it can be inferred from the not limiting described examples. Therefore the modulation of the parameters of the reaction makes it possible to obtain compounds more or less deeply modified in their structure.

The amount of the chemical modification can be calculated by doing the ratio between the sum of the integrals of the peaks at about 53 and about 54 ppm and the sum of the integrals of the peaks of the carbon atom in the position 6 of the glucosamine unit, at about 62.5 and about 69 ppm, these latter being selected as an arbitrary reference because their intensity remains stable and because they are in a spectrum zone free from other peaks. Together with the increase of the resonances at about 53 and about 54 ppm there is an increase of the rotatory power at 589 nm (D line of sodium) and therefore the measurement of the specific rotatory power can be directly used for the evaluation of the degree of the chemical modification occurred in the heparinic structure. As optically active reagents are not used in the reaction medium, the measurement of the rotatory power can be directly used for the check of the course of the reaction.

Both the ratios of the integrals of the peak of the $^{13}$C-NMR and the increase of the specific rotatory power in respect of the starting compound are reported in the following table 1.

TABLE 1

| EXAMPLE | Area of peaks at 53 and 54 ppm / Area of peaks at 62.5 and 69 ppm | Difference among the specific rotatory powers of the modified and the starting heparins $[\alpha]_D^{20}$ |
|---|---|---|
| 5 | 0.15 | +5° |
| 6 | 0.25 | +7° |
| 7 | 0.30 | +7° |
| 4 | 0.45 | +10° |
| 1 | 0.55 | +18° |
| 2 | 0.75 | +22° |
| 3 | 1.20 | +29° |

These modified heparins are moreover characterized in that they possess a different electrophoretic behaviour from that of the starting compounds, characterized by a greater mobility in barium acetate buffer 0.1M at pH 5.8 [P. Oreste, G. Torri, J. Chrom. 195, 398, (1980)], and in that they have a sulfur content between about 8% and about 11%, a sulfates/carboxyls ratio between about 1.50 and about 2.20 and a specific rotatory power $[\alpha]_D^{20}$ between about +50° and about +90° as it is shown by the following table 2 where, in brackets, the values of the corresponding starting compounds are reported.

TABLE 2

| EXAMPLE | % sulfates | sulfates/carboxyls ratio | $[\alpha]_D^{20}$ |
|---|---|---|---|
| 5 | 10.31 (11.40) | 2.17 (2.27) | +50° (+45°) |
| 6 | 10.69 (11.60) | 2.15 (2.32) | +54° (+47°) |
| 7 | 9.70 (11.00) | 1.90 (2.00) | +51° (+44°) |
| 4 | 9.65 (10.56) | 2.03 (2.20) | +57° (+47°) |
| 1 | 8.95 (10.56) | 1.94 (2.20) | +65° (+47°) |
| 2 | 8.42 (10.09) | 1.64 (2.13) | +65° (+43°) |
| 3 | 8.12 (10.09) | 1.56 (2.13) | +72° (+43°) |

The new heparin derivatives, object of the present invention, possess a marked antithrombotic activity together with a lower anticoagulant activity in respect of the starting heparins. Their biological activity was assessed through many typical tests of the heparins; precisely the tests of the anti-Xa factor, of APTT, of the bleeding time and of the protection from the experimental thrombosis were carried out. The APTT activity was determined according to the method of Larrieu M. J. and Weiland G., Rev. Hematol., 12, 199, (1957), while the anti-Xa activity was determined according to the method of Yin E. T. and Wessler S., Biochem. Biophys. Acta, 201, 387, (1970).

Every examined compound was dissolved in plasma taken from fasting rats, then proportional dilutions were made to obtain the concentrations provided for by the method. Ten determinations were performed for both activities for each compound and the quantity that causes a highly significant change in the corresponding test was calculated in mcg/ml. In particular, the activity of each product was expressed as the concentration, in mcg/ml, that respectively doubles the APTT time and that increases the anti-Xa value of 30%. The values obtained in the two tests (see table 3) confirm that the new compounds show a diminution of the anticoagulant power.

The bleeding time was carried out in the rat according to the method described by Dejana E. et al, Thromb. Haemost., 48, 108, 1982 and the result was expressed by calculating the percent of the time of the bleeding elongation in the rats treated with the new heparins in comparison with the time of bleeding elongation in the rats treated with the corresponding starting heparins considered equal to 100%. All the new derivatives having modified heparinic structure, object of the present invention, showed a decrease, often very marked, of the bleeding time, in comparison with the corresponding starting heparins.

The antithrombotic activity was assessed by the test of the stasis venous thrombosis described by Reyers S. et al. Thromb. Res. 18, 669-74, 1980. The protection afforded by the new compounds was calculated, in percent, by taking equal to 100 the antithrombotic protection given by the starting heparins.

The obtained results showed a substantial equivalence of the two series of heparins as regards this test on the antithrombotic activity.

The values of the above described biological tests are summarized in the following table 3 where the anti-Xa and the APTT values of the corresponding starting heparins are reported within brackets.

TABLE 3

| EXAMPLE | Anti-Xa Activity Amount of compound which increases the anti-Xa value of 30% (mcg/ml) | APTT Activity Amount of compound which doubles the APTT time (mcg/ml) | Bleeding time. % Elongation in comparison with the starting heparinic material | Antithrombotic protection % in comparison with the starting heparinic material |
|---|---|---|---|---|
| 1 | 30.2 (20.6) | 4.2 (1.7) | 22 | 100 |
| 2 | 33.7 (18.6) | 8.9 (1.9) | 83 | 117 |
| 3 | 43.5 (18.6) | 16.3 (1.9) | 11 | 53 |
| 4 | 18.1 (20.6) | 4.8 (1.7) | 60 | 75 |
| 5 | 21.0 (16.5) | 11.5 (10.8) | 9 | 113 |
| 6 | 44.0 (40.6) | 8.8 (8.5) | 30 | 113 |
| 7 | 19.6 (18.2) | 2.6 (2.0) | 30 | 88 |

In view of the above seen pharmacological properties, these new heparin derivatives are useful for treating thrombotic diseases. The preferred ways of administration are the parenteral and the subcutaneous ones in form of sterile aqueous solutions, optionally containing also some salts, in order to make the solution isotonic, and some preserving agents.

The dosage range depends on the used pharmaceutical formulations and on the state of the patient; in a preferred way, an amount of heparin derivative, according to the present invention, equivalent to between 5,000 and 20,000 Units of anti-Xa factor (U.A. Xa) is administered one or more times a day.

As the starting substrates, heparinic materials of different origin can be employed. For example, commercial heparins and heparins purified by treatment of commercial heparins, as well as low molecular weight heparins, obtained by depolymerization according to methods known in the art, were employed in order to get the modified heparins object of the present invention. Underneath, we show the preparation of the starting heparinic materials used in the present invention.

Sodium heparin ALFA 87-78

25 Grams of commercial sodium heparin are dissolved in 2000 ml of water and poured in about 30 minutes into a solution containing 111.2 g of calcium acetate monohydrate in 2000 ml of water, 57 ml of acetic acid and 600 ml of ethyl alcohol, while keeping the temperature at about $8° \div 10°$ C. The obtained suspension is filtered after 15 hours at 5° C. and the filtrate is added with 1000 ml of ethyl alcohol and after 3 hours at 5° C. the obtained precipitate is filtered. The precipitate is then dissolved in 200 ml of water, the solution is brought to pH 7.0 by means of sodium hydroxide 1N and then it is treated with 100 ml of Dowex 50W×8, sodium form, resin and with 70 ml of water for 20 minutes. Solution and resin are transferred into a chromatograpphic column ($\phi=1.6$ cm, h=10 cm) containing 80 ml of the same resin. After having percolated the solution and eluted it with distilled water until a total volume of solution equal to 400 ml, to the solution is added 12 g of sodium acetate trihydrate and with 1000 ml of ethyl alcohol. The precipitate is filtered and dried under vacuum obtaining 19.2 g of purified sodium heparin named ALFA 87-78 having the following chimico-physical characteristics:

S=10.09%, sulfates/carboxyls ratio=2.13,
$[\alpha]_D^{20}= +43°$ (C=1% in H$_2$O)
$^{13}$C-NMR spectrum (ppm): 177.3; 104.7; 102.0; 99.4; 80.0; 78.6; 72.3; 71.9; 69.0; 62.5; 60.6.

Sodium heparin ALFA 87-81

It was obtained by means of the same method of purification used for ALFA 87-78 starting from 50 g of the same commercial heparin.

36,5 Grams of purified heparin were obtained having the following chimico-physical characteristics:

S=10,56%; sulfates/carboxyls ratio=2.20
$[\alpha]_D^{20}= +47°$ (C=1% in H$_2$O)
$^{13}$C-NMR spectrum (ppm): 177.3; 104.7; 102.0; 99.5; 80.1; 78.6; 72.4; 72.0; 69.1; 62.7; 60.7.

Commercial sodium heparin

It is a heparin having the following chimico-physical characteristics:

S=11.0%; sulfates/carboxyls ratio=2
$[\alpha]_D^{20}= +44°$ (C=1% in H$_2$O)
$^{13}$C-NMR spectrum (ppm): 177.4; 104.6; 101.9; 99.8; 79.9; 78.6; 72.2; 71.8; 69.0; 62.6; 60.6.

Low molecular weight sodium heparin LMW ALFA 86-02

The low molecular weight sodium heparin LMW ALFA 86-02 was prepared by depolymerization with hydrogen peroxide in presence of cupric ions according to the method described in the international patent publication WO No. 86/06729.

It shows the following chimico-physical characteristics:

average molecular weight: 4200 daltons,
S=11.40%; sulfates/carboxyls ratio=2.27
$[\alpha]_D^{20}= +45°$ (C=1% in H$_2$O)
$^{13}$C-NMR spectrum (ppm): 177.4; 104.6; 101.9; 99.8; 79.9; 78.6; 72.6; 72.2; 71.9; 69.1; 62.7; 60.7.

Low molecular weight sodium heparin LMW ALFA
87-198

The low molecular weight sodium heparin LMW ALFA 87-198 was prepared by depolymerization according to the method used for LMW 86-02.

It shows the following chimico-physical characteristics:

S=11.60%; sulfates/carboxyls ratio=2.32
$[\alpha]_D^{20} = +47°$ (C=1% in H$_2$O)
$^{13}$C-NMR spectrum (ppm): 177.7; 104.8; 102.0; 99.6; 80.2; 78.6; 72.4; 71.9; 69.2; 62.7; 60.6.

The determination of the values of the specific rotatory power $[\alpha]_D^{20}$ was carried out in aqueous medium at a concentration of 1%.

The determination of the sulfates/carboxyls ratio was executed by potentiometric way.

The determination of the sulfur percentage was carried out both with the potentiometric method and with the Schoeniger method.

The $^{13}$C-NMR spectra were executed at 75.47 MHz with a Varian CFT-75 spectrometer by using D$_2$O as solvent and sodium 3-trimethylsilylpropansulfonate as reference internal standard.

The following examples have to be considered as an explanation of the present invention and not as an its limitation.

EXAMPLE 1

1.8 Grams of heparin ALFA 87-81 are added to 45 ml of an aqueous solution containing 0.4 g of sodium hydroxide (0.225N), 2.3 g of sodium acetate (0.625N) and 10 mg of sodium borohydride. The obtained solution is thermostated at 60° C. for 3.5 hours, then it is cooled to room temperature, brought to neutrality with glacial acetic acid and added to 2.5 volumes of ethanol. The precipitate is filtered, washed on the filter with a 6:1 ethanol/water mixture and dried. 1.7 Grams of product are obtained having a $^{13}$C-NMR spectrum that shows characteristic signals at the following δ (expressed as ppm): 177.3; 104.3; 101.9; 99.4; 98.4; 97.2; 96.8; 79.7; 79.1; 78.5; 72.1; 71.8; 71.2; 68.8; 62.4; 60.6; 60.3; 54.1; 53.1.

EXAMPLE 2

1.8 Grams of heparin ALFA 87-78 are added to 45 ml of an aqueous solution containing 0.4 g (0.225N) of sodium hydroxide, 2.3 g of sodium acetate (0.625N) and 10 mg of sodium borohydride. The solution is thermostated at 60° C. for 15 hours and, after cooling, it is brought to neutrality with acetic acid and then it is percolated through a column ($\phi$=1.2 cm, h=8 cm) containing Dowex 1×2, chloride form, anionic resin. The percolate and the washings are collected together and added to 2.5 volumes of ethanol. The precipitate is filtered, washed on the filter with a 6:1 ethanol/water mixture and dried. 1.65 Grams of product are obtained having a $^{13}$C-NMR spectrum that shows characteristic signals at the following δ (expressed as ppm): 177.4; 104.6; 101.8; 98.6; 97.2; 96.8; 79.6; 79.1; 78.9; 72.2; 71.5; 71.2; 68.8; 62.5; 60.3; 54.1; 53.1.

EXAMPLE 3

1.8 Grams of heparin ALFA 87-78 is added to 120 ml of an aqueous solution containing 4.8 g (1N) of sodium hydroxide. The solution is thermostated at 60° C. for 3.5 hours, brought to neutrality with acetic acid and dialyzed for one night with running water and for 6 hours with distilled water. The solution is then added to 3.5 g of sodium acetate, brough to neutrality with acetic acid and added to 2.5 volumes of ethanol. The precipitate is filtered, washed with a 6:1 ethanol/water mixture and dried. 1.7 Grams of product are obtained having a $^{13}$C-NMR spectrum that shows characteristic peaks a the following δ (expressed as ppm): 177.4; 104.6; 101.7; 98.6; 98.4; 97.2; 96.8; 79.7; 79.1; 78.6; 73.5; 72.5; 72.3; 72.1; 71.5; 68.8; 62.6; 60.4; 60.2; 54.0; 53.1.

EXAMPLE 4

4 Grams of heparin ALFA 87-81 are added to 120 ml of an aqueous solution containing 4.8 g (1N) of sodium hydroxide, 6.2 g (0.625N) of sodium acetate and 25 mg of sodium borohydride. The reaction mixture is thermostated at 60° C. for 3.5 hours, then it is neutralized with acetic acid, dialyzed for 24 hours with running water and percolated through a Dowex 1×4, chloride form, anionic resin ($\phi$=1.6 cm, h=15 cm). The percolate and the washings are added to 4 g of sodium acetate and 2.5 volumes of ethanol. The precipitate is filtered and washed on the filter with a 6:1 ethanol/water mixture and dried. 3.55 Grams of product are obtained having a $^{13}$C-NMR spectrum that shows characteristic peaks at the following δ (expressed as ppm): 177.4; 104.5; 101.8; 99.4; 98.7; 97.1; 79.5; 78.6; 73.5; 71.8; 68.8; 62.4; 60.3; 54.0; 53.1.

EXAMPLE 5

1.8 Grams of heparin LMW ALFA 86-02 are added to 50 ml of an aqueous solution containing 0.08 g (0.04N) of sodium hydroxide, 2.6 g (0.625N) of sodium acetate and 10 mg of sodium borohydride. The reaction mixture is thermostated at 60° C. for 210 minutes, then it is cooled to room temperature and is percolated first on a column of anionic resin Dowex 1×4, OH$^-$ form ($\phi$=1.2 cm, h=10 cm) and then on a column of cationic resin Dowex 50 W×8, H$^+$ form ($\phi$=1.2 cm; h=10 cm). The percolate and the washings are brough to neutrality by means of a 2N aqueous solution of sodium hydroxide and then are added with 4 g of sodium acetate and with 2.5 volumes of ethanol.

The obtained precipitate is washed with a 6:1 ethanol/water mixture and dried. 1.4 Grams of product are obtained having a $^{13}$C-NMR spectrum that shows characteristic peaks of the following δ (expressed as ppm): 177.4; 104.6; 101.9; 99.4; 98.6; 98.4; 97.2; 96.8; 79.9; 78.6; 72.3; 71.9; 68.8; 62.6; 60.3; 54.1; 53.1.

EXAMPLE 6

10 Grams of heparin LMW ALFA 87-198 are added to 300 ml of an aqueous solution containing 2.7 g (0.225N) of sodium hydroxide, 15 g (0.625N) of sodium acetate and 60 mg of sodium borohydride. The solution is thermostated at 60° C. for 50 minutes, cooled to room temperature, diluted to 500 ml with distilled water and percolated first on anionic resin Dowex 1×2, OH$^-$ form ($\phi$=2 cm; h=15 cm) and then on cationic resin Dowex 50 W×8, H$^+$ form ($\phi$=2 cm; h=15 cm). The percolate and the washings are brought to neutrality by means of a 4N aqueous solution of sodium hydroxide and then are added with 20 g of sodium acetate and 2.5 volumes of ethanol. The obtained precipitate is washed with a 6:1 ethanol/water mixture and dried. 9.1 Grams of product are obtained having a $^{13}$C-NMR spectrum that shows characteristic peaks at the following δ (expressed as ppm): 177.4; 104.6; 101.9; 99.8; 98.6; 98.4;

97.2; 96.8; 79.8; 78.6; 72.2; 71.8; 68.9; 62.5; 60.3; 54.1; 53.1.

EXAMPLE 7

15 Grams of commercial sodium heparin are added to 600 ml of an aqueous solution containing 5.4 g (0.225N) of sodium hydroxide, 30 g (0.625N) of sodium acetate and 120 mg of sodium borohydride. The solution is thermostated at 42° C. for 4 hours, cooled at room temperature and brough to netrality with acetic acid. The solution is dialyzed for one night with running water and then is percolated on a column of anionic resin Dowex 1×2, chloride form ($\phi$=2.8 cm; h=15 cm). The percolate and the washings are added to 10 g of sodium acetate, brought to pH 7 by means of a 2N aqueous solution of sodium hydroxide and added to 2.5 volumes of ethanol. The obtained precipitate is washed with a 6:1 ethanol/water mixture and dried. 13.9 Grams of product are obtained having a $^{13}$C-NMR spectrum that shows characteristic peaks at the following $\delta$ (expressed as ppm): 177.3; 104.6; 101.9; 99.8; 98.6; 98.4; 97.2; 96.8; 79.9; 78.6; 72.2; 71.8; 69.0; 62.5; 60.3; 54.1; 53.1.

EXAMPLE 8

A vial for parenteral use contains:

| | |
|---|---|
| heparin modified according to Example 1 | 10.000 U.A.Xa |
| F.U. sodium chloride F.U. | 5 mg |
| B.P Benzyl alcohol | 8 mg |
| bidistilled sterile water | 1 ml |

We claim:

1. A heparin derivative which exhibits signals in the $^{13}$C-NMR spectrum at about 53 and about 54 ppm, specific rotatory power $[\alpha]^{20}$ between about +50° and about +90° in aqueous solution, sulfur content between about 8% and about 11% and sulfate/carboxyl ratio between about 1.50 and about 2.20.

2. The heparin derivative according to claim 1 which is derived from a heparinic material having a glucosamine unit, wherein said heparin derivative has a molecular weight essentially as said heparinic material, and which exhibits signals in the $^{13}$C-NMR spectrum in the region between 92 ppm and 102 ppm and in which signals related to position 2 of the glucosamine units of said heparinic material are unchanged.

3. The heparin derivative according to claim 2 which is derived from a heparinic material selected from the group consisting of:
(a) commercial sodium heparin of sulfate/carboxyl ratio of 2 and specific rotatory power +44°;
(b) a low molecular weight sodium heparin of sulfate/carboxyl ratio of 2.27 and specific rotatory power +45°;
(c) a low molecular weight sodium heparin of sulfate/carboxyl ratio 2.32 and specific rotatory power +47°;
(d) a purified heparin of sulfate/carboxyl ratio 2.20 and specific rotatory power +47° and
(e) a purified heparin of sulfate/carboxyl ratio 2.13 and specific rotatory power +43°.

4. A process for the preparation of a heparin derivative which exhibits signals in the $^{13}$C-NMR spectrum at about 53 and about 54 ppm, specific rotatory power between about +50° and about +90° in aqueous solution, sulfur content between about 8% and about 11% and sulfate/carboxyl ratio between about 1.50 and about 2.20 which comprises the steps of: (a) treating a heparinic material with an aqueous solution of a base which is an alkali or alkaline earth metal hydroxide of a concentration between about 0.01N and about 1N for a period of time between 0.5 and 24 hours at a temperature between about 35° C. and about 60° C. to obtain a reaction mixture; (b) purifying said reaction mixture by percolation through an ion exchange resin or by dialysis; and (c) precipitating said heparin derivative by adding from about 2 to about 4 volumes of an alcohol containing from 1 to 3 carbon atoms at about a neutral pH.

5. The process according to claim 4 wherein in step (a) a salt of an alkali or alkaline earth metal is added in a concentration up to 1N.

6. The process according to claim 4 wherein in step (a) a reducing agent is added in a concentration of 0.5–0.8% with respect to said heparinic material.

7. The process according to claim 5 wherein in step (a) a reducing agent is added in a concentration of 0.5 and 0.8% with respect to said heparinic material.

8. The process according to claim 7 wherein the base is sodium, potassium or barium hydroxide.

9. The process according to claim 5 wherein the salt is a member selected from the group consisting of sodium, potassium, barium, calcium and magnesium chlorides and acetates and sodium, potassium and magnesium sulfates.

10. The process according to claim 6 wherein the reducing agent is sodium borohydride.

11. The process according to claim 7 wherein the reducing agent is sodium borohydride.

12. The process according to claim 4 wherein said heparin derivative is precipitated in step (c) by adding about 2.5 volumes of ethyl alcohol.

13. The method of treating a patient suffering from a thrombotic disease which consists of administering to said patient a therapeutically effective amount of a heparin derivative according to claim 1 containing between about 5,000 and about 20,000 units of anti-Xa factor (U.A.Xa) one or more times a day.

14. A pharmaceutical composition with antithrombotic activity containing as the active ingredient 10,000 U.A.Xa units of the heparin derivative according to claim 1 in an isotonic aqueous solution, containing at least one salt and at least one preservative.

* * * * *